(12) United States Patent
Hansen et al.

(10) Patent No.: US 11,291,886 B2
(45) Date of Patent: Apr. 5, 2022

(54) VIRTUAL TRAINING ENVIRONMENT FOR CYCLING AND OTHER ATHLETIC ACTIVITIES

(71) Applicant: Intelligent Training Group ApS, Sorø (DK)

(72) Inventors: Peter Møller Hansen, Sorø (DK); Brian Overkær, Sorø (DK); Anders Willemoes Hansen, Sorø (DK)

(73) Assignee: Intelligent Training Group ApS, Sorø (DK)

( * ) Notice: Subject to any disclaimer, the term of this patent is extended or adjusted under 35 U.S.C. 154(b) by 97 days.

(21) Appl. No.: 16/598,625

(22) Filed: Oct. 10, 2019

(65) Prior Publication Data
US 2021/0106875 A1     Apr. 15, 2021

(51) Int. Cl.
*A63B 24/00* (2006.01)

(52) U.S. Cl.
CPC ...... *A63B 24/0075* (2013.01); *A63B 24/0006* (2013.01); *A63B 24/0062* (2013.01); *A63B 2024/0065* (2013.01); *A63B 2024/0068* (2013.01)

(58) Field of Classification Search
None
See application file for complete search history.

(56) References Cited

U.S. PATENT DOCUMENTS

| | | | |
|---|---|---|---|
| 7,695,406 B2 * | 4/2010 | Waters | A63F 13/10 482/8 |
| 9,174,085 B2 | 11/2015 | Foley et al. | |
| 2006/0030405 A1 * | 2/2006 | Robertson | A63F 13/10 463/30 |
| 2009/0227429 A1 * | 9/2009 | Baudhuin | A63B 24/0062 482/57 |
| 2010/0035726 A1 * | 2/2010 | Fisher | A63B 24/0084 482/8 |
| 2011/0172059 A1 * | 7/2011 | Watterson | A63B 24/0062 482/5 |
| 2012/0237911 A1 * | 9/2012 | Watterson | A63B 24/0087 434/247 |

(Continued)

FOREIGN PATENT DOCUMENTS

EP     2672476 A1     12/2013

*Primary Examiner* — Sundhara M Ganesan
*Assistant Examiner* — Shila Jalalzadeh Abyaneh
(74) *Attorney, Agent, or Firm* — Dinsmore & Shohl LLP (57) ABSTRACT

A method provides an interactive training environment for athletic activities performed on an exercise device. A workout plan is selected or generated, having a plurality of sequential intervals, each having at least one training parameter, such as intensity. A virtual training world is generated, having a virtual training surface divided into a plurality of sequential intervals, each interval having an inclination that is a function of the training parameter associated with the respective intervals of the workout plan. World features, which may include turns in the training surface, may be pseudo-randomly generated. A visual representation of the virtual training world is displayed and represents a participant position in the virtual training world. The participant position is synchronized based on speed, distance traveled, or elapsed time. Feedback indicia are displayed to the participant, such as interval markers indicating borders or transitions between the sequential intervals.

21 Claims, 5 Drawing Sheets

(56) References Cited

U.S. PATENT DOCUMENTS

2016/0250519 A1* 9/2016 Watterson .......... A63B 24/0075
  482/4
2017/0354845 A1* 12/2017 Williams ................ A61B 5/11
2019/0151714 A1 5/2019 Baudhuin
2020/0254311 A1* 8/2020 Watterson .......... A63B 71/0622

* cited by examiner

VIRTUAL TRAINING ENVIRONMENT FOR CYCLING AND OTHER ATHLETIC ACTIVITIES

FIELD OF THE INVENTION

The present invention generally relates to providing an interactive training environment for athletic activities.

BACKGROUND OF THE INVENTION

Athletic activities, such as cycling and running, typically take place outside. Training for such activities often takes place indoors, using exercise devices such as stationary bikes, training devices that attach to a bicycle, or treadmills. One popular type of bicycle-based training takes the form of indoor cycling classes where a plurality of participants pedal stationary bikes while being directed by an instructor. The stationary bikes mimic real bikes in that they include pedals, a seat, and handle bars, and further include some type of adjustable resistance mechanism to provide variable resistance levels. The instructor typically coaches the class through a workout plan having a plurality of sequential intervals. During each interval, the class will be instructed to use a particular exercise position (seated or one or more standing positions) at a particular pace (an RPM or cadence) and at a resistance level. The resistance level may be a specific resistance level or a resistance level that the participant perceives as corresponding to the instructor's instructions. For example, the instructor may ask the class to pedal for one minute at an RPM of 70 to 80 with medium-high resistance. The precise resistance level used by each participant is typically chosen by the participant and may vary widely from participant to participant, depending on the individual participant's fixed level and how they are feeling.

While in-person cycling classes are very popular, distributed and/or virtual training classes are becoming increasingly popular. In one example, an instructor is in a first location while one or more participants are located at one or more remote locations. The instructor communicates with the students using video and audio, such as through an internet webpage. Alternatively, dedicated software may be used to provide communication between the instructor and participants. The class proceeds similarly to an in-person class except that the participants and the instructor are remote from one another. U.S. Pat. No. 9,174,085 to Foley et al. discloses an example of a method for providing cycling classes to remote participants. Similar training classes are available for runners using treadmills either for in-person classes or remote training.

Another popular approach to indoor training is the provision of virtual training environments. One example is Zwift™ which provides a virtual "world" in which participants may cycle or run. Participants use an indoor bike or treadmill to participate. Many participants use a cycle trainer, which is a device that attaches to the rear wheel or drivetrain of a bicycle and provides variable resistance levels to a participant. Software provides for two-way communication between the virtual "world" and the exercise equipment. The participant's speed, cadence, power output and other factors may be communicated to a remote server and the participant's position within the virtual "world" is adjusted to provide semi-realistic correspondence between the participant's effort and movement in the world. Depending on the equipment being used by the participant, the remote server may also communicate control signals to the exercise device that causes the exercise device to adjust resistance. The communication protocol may be Bluetooth or Ant+. For example, when the participant comes to a virtual incline in the virtual world, the server may communicate to the exercise equipment to increase the resistance level. Alternatively, the participant may manually adjust the resistance level of their equipment to coordinate their effort with their apparent position in the virtual world. In this example, the virtual world allows for a very large number of participants to "ride" or "run" in the same virtual world and to perceive avatars of each other representing their relative positions and speeds. Communication between remote participants is also allowed. However, the virtual world is fixed, in the sense that the path or road to be traveled by the avatar is the same each time the participant visits the virtual world. A large number of possible roads and paths may be provided, but each path or road is the same, visit to visit. Features within the virtual world vary during exercise sessions and between sessions, such as the weather, sounds, and the apparent position of the sun. Certain virtual training systems also allow for training plans wherein the resistance level experienced by the participant is predefined so as to provide a specified sequence of intervals. For example, a participant who is training for speed may make use of a training plan including a plurality of high speed "sprints" separated by recovery periods. A participant who is training for climbing may use a plan having a plurality of high effort, low cadence intervals separated by recovery periods.

SUMMARY OF THE INVENTION

A method for providing an interactive training environment for athletic activities may be performed on an exercise device with variable resistance levels. The following steps may be performed on a computer. A workout plan is selected or generated, having a plurality of sequential intervals, each interval having at least one training parameter associated therewith, the at least one training parameter including an intensity. A new virtual training world is generated, having a virtual training surface, the training surface divided into a plurality of sequential intervals, each interval having an inclination/steepness that is a function of the at least one training parameter associated with a respective one of the intervals of the workout plan, the virtual training world further having a plurality of world features including at least turns in the training surface, at least some of the plurality of world features being pseudo-randomly generated each time a new virtual training world is generated. A visual representation of the virtual training world is displayed, the visual representation representing a participant position in the virtual training world. The participant's position in the virtual world is synchronized based on a speed of and/or distance traveled by the participant and/or an elapsed time. At least one feedback indicia is displayed to the participant, the feedback indicia being selected from interval markers indicating borders or transitions between the sequential intervals of the training surface and one of the training parameters.

In some versions, the at least one training parameter further includes a pace and/or an exercise position. The pace may be an RPM or a cadence and the exercise position may be a seated position or one or more standing positions. RPM and cadence are synonymous in the following.

In some versions, the method further includes initiating, by a participant, a selected or generated workout session, the generating a new virtual training world step being performed after the initiating step and before the displaying step.

In some versions, the step of selecting or generating a workout comprises generating a workout by defining the plurality of sequential intervals, the at least one training parameter associated with at least some of the intervals including the intensity, an RPM or cadence, and an exercise position.

In some versions, the method further includes providing from the computer an intensity signal operable to adjust the variable resistance levels of the exercise device.

In some versions, the feedback indicia include the interval markers, the interval markers being color-coded and/or pattern-coded to differentiate the intervals.

In some versions, the training surface following each interval marker is at least partially color-coded or pattern-coded to match the corresponding interval marker.

In some versions, the feedback indicia further include at least one of total training time, time remaining in interval, time remaining in workout, target RPM, target RPM range, target intensity, exercise position, resistance level of the exercise device, actual participant RPM, actual participant heart rate, and actual participant wattage.

In some versions, the step of displaying feedback indicia includes displaying an intensity level corresponding to the inclination of the training surface.

In some versions, the method further includes receiving by the computer a signal from the exercise device representing a speed or and/or a distance traveled by the participant.

In some versions, the world features further include at least one feature selected from a group consisting of weather, wind, animals, plants, landscape features, sounds and people.

In some versions, the inclination is a function of intensity, pace and position.

In some versions, the function comprises defining a height of an endpoint of a tile, the height being determined from a lookup table.

In some versions, the computer further includes an AI system configured to interpret the at least one training parameter and associate the at least one training parameter to the training system and the plurality of world features.

In some versions, the selecting or generating a workout plan includes generating a workout plan and saving the workout plan.

In some versions, the computer includes at least a first computer for generating the workout plan and a second computer for displaying the visual representation.

In some versions, the plurality of world features that are pseudo-randomly generated includes the turns.

An apparatus for providing an interactive training environment for athletic activities performed on an exercise device with variable resistance levels, includes a memory and at least one processor, coupled to the memory, operative to perform the following steps: selecting or generating a workout plan having a plurality of sequential intervals, each interval having at least one training parameter associated therewith, the at least one training parameter including an intensity; generating a new virtual training world having a virtual training surface, the training surface divided into a plurality of sequential intervals, each interval having an inclination that is a function of the at least one training parameter associated with a respective one of the intervals of the workout plan, the virtual training world further having a plurality of world features including at least turns in the training surface, at least some of the plurality of world features being pseudo-randomly generated each time a new virtual training world is generated; displaying a visual representation of the virtual training world, the visual representation representing a participant position in the virtual training world; synchronizing the participant position in the virtual world based on a speed of and/or distance traveled by the participant and/or an elapsed time; displaying at least one feedback indicia to the participant, the feedback indicia being selected from interval markers indicating borders or transitions between the sequential intervals of the training surface and one of the training parameters.

A machine readable storage medium containing one or more programs, for providing an interactive training environment for athletic activities performed on an exercise device with variable resistance levels, may perform the steps of: selecting or generating a workout plan having a plurality of sequential intervals, each interval having at least one training parameter associated therewith, the at least one training parameter including an intensity; generating a new virtual training world having a virtual training surface, the training surface divided into a plurality of sequential intervals, each interval having an inclination that is a function of the at least one training parameter associated with a respective one of the intervals of the workout plan, the virtual training world further having a plurality of world features including at least turns in the training surface, at least some of the plurality of world features being pseudo-randomly generated each time a new virtual training world is generated; displaying a visual representation of the virtual training world, the visual representation representing a participant position in the virtual training world; synchronizing the participant position in the virtual world based on a speed of and/or distance traveled by the participant and/or an elapsed time; and displaying at least one feedback indicia to the participant, the feedback indicia being selected from interval markers indicating borders or transitions between the sequential intervals of the training surface and one of the training parameters.

DETAILED DESCRIPTION OF THE INVENTION

The embodiments of the present invention include a method for providing an interactive training environment for athletic activities on an exercise device with variable resistance levels. Exemplary exercise devices may include a stationary bike, a trainer that attaches to a bike so as to provide resistance, and a treadmill. A participant or participants may generate a workout plan or may select a pre-designed workout plan. Such a workout plan has a plurality of sequential intervals. Each of the intervals has at least one training parameter associated with the interval. Examples of training parameters include intensity, pace, exercise position, duration of the interval, and whether the various parameters are held constant during the interval or are increased or decreased. As a non-limiting example, a particular interval may have a moderate intensity level, a fast pace, may be performed while seated (on the stationary bike or bicycle attached to the trainer), may last for one minute and all parameters are held constant during this interval. As known to those of skill in the art, intensity level may be specified in a variety of ways. Examples include a percentage of Functional Threshold Power (% FTP), a percentage of maximum heart rate (% HRMAX) or a Rate Perceived Exertion (RPE). Further examples include percentage of Maximum Aerobic Power (% MAP), percentage of Functional Threshold Heart Rate (% FTHR), percentage of Lactate Threshold Heart Rate (% LTHR), percentage of VO2MAX (% VO2MAX), Coggan Power Zones, and various exertion scales. A number of other approaches are available for specifying an intensity level, including more descriptive indicators such as medium, medium-hard, hard, maximum, etc., or abstract indicators such as red (hard) and green (easy).

A workout plan includes a plurality of these intervals sequentially arranged such that the intervals together define a workout plan or a workout session. Some intervals may have a high intensity level while others have a low intensity level, and any of the training parameters may vary interval to interval. Some intervals may have more defined training parameters than others. For example, a recovery interval may merely indicate that the intensity level is "recovery" without specifying a pace, a position or other parameters.

Different workout plans may have different purposes. As one example, a workout plan may be designed to help a participant train for speed and therefore include various high speed intervals interspersed with recovery periods. Alternatively, a plan may help a participant train for climbing and include a plurality of high-intensity and low-pace intervals interspersed with low exertion or recovery intervals.

A variety of approaches may be taken to designing or generating a workout plan, some of which will be discussed hereinbelow. A method of the present invention may allow a participant to select from a variety of workout plans including plans generated by other participants, trainers and workouts previously generated by the participant and saved for future use. Workout plans may be grouped into training camps that include a plurality of workout sessions that share certain similarities or that are intended to be used in a particular order, such as training for a particular event.

After a participant has selected or generated a workout plan, a virtual training world is computer-generated. This virtual training world is referred to as a "new" virtual training world because, in preferred embodiments, a virtual training world is generated for each individual use by a participant such that the participant is always presented with a different training world. The virtual training world has a virtual training surface, representing a road or path, with the training surface divided into a plurality of sequential intervals. Each interval has an inclination that is a function of the training parameters associated with one of the intervals of the workout plan. For example, a first interval of the selected or generated workout plan will have one or more training parameters and these training parameters are used by the computer to define an inclination for the first interval of the training surface in the virtual training world. As a further example, a high-intensity interval of the workout plan will correspond to a steep inclination of the training surface in the corresponding interval in the virtual training world, while a low-intensity or low effort interval of the workout plan will have a lower inclination training surface in a corresponding interval of the virtual training world. The term "inclination" as used herein may include flat surfaces and descending surfaces. A surface that rises has a higher inclination than a flat or descending surface, but each of the surfaces may be associated with a resistance level greater than zero, depending on the parameters used. The virtual training surface preferably is continuous in that the surface at the end of one interval smoothly transitions into the training surface of the beginning of the next training interval. For example, a high inclination training surface of one interval may flow into a nearly flat or downhill inclination training surface for a lower effort subsequent interval.

In one embodiment of the present invention, the training surface is divided into intervals, which may also be called segments or tiles. Alternatively, an interval may be divided into multiple tiles. Each tile represents a certain distance, and has a start point and an end point. If the tile represents a full interval, the start and end would coincide with interval markers. The tangents of the tiles may match each other so that a transition from one tile to another is smooth. The part of the overall training surface of path between a start and an end point of a tile may be determined by a spline function.

In one example, the height of the end point, relative to the start point, is what is determined. A lower cadence results in a higher end point. A standing position, versus a sitting position, results in a higher end point. A higher intensity results in a higher end point. A lookup table may be used so that, for example, when the cadence is within a specific interval, and the position is standing, and the intensity is within a specific interval, the height of the end point is provided by the table. As such, a single height of an end point may be provided by more than one combination of cadence, position and intensity.

In order to provide visual interest to the participant, the virtual training world is designed to be rich with world features, some or all of which are pseudo-randomly generated each time a new virtual training world is generated. The term "pseudo-random" as used herein means that the features are not predetermined but are instead generated as part of a generally random process, which recognizing that such "random processes" may not be entirely random in a mathematical sense.

Examples of world features include turns in the training surface, colors, weather, wind, animals (including movement of the animals), plants, landscape features, sounds and virtual persons. The appearance of the training surface may also be pseudo-randomly generated or may be selected by a participant. In some examples, the training surface may appear to be a ribbon of water on which the participant virtually rides or runs. The generation of the virtual training world may be started when a participant initiates a selected or generated workout session. In some examples, the turns and their features (radius, total degrees of turning, banking, etc.) are deterministic, such as being provided by a lookup table, which in other examples some or all of the turns, or features of the turns, are pseudo-randomly generated.

Once a new virtual training world has been generated, a visual representation of the virtual training world is displayed, such as on a computer screen, television, or virtual or augmented reality eyewear. A participant's position in the virtual world is synchronized so as to provide the appearance of moving through the virtual training world by travelling along the virtual training surface. This synchronization may be accomplished in a variety of ways. As one example, the participant will appear to move through one interval in the amount of time designated for that interval, such as one minute. This is an approach based on elapsed time. Alternatively, the exercise device used by the participant may provide feedback, such as a signal indicating speed or intensity or other information, to the system so as to provide the speed of and/or distance traveled by the participant and this information may be used to update the displayed position of the participant. The participant's position may be represented in the virtual training world by showing an avatar moving along the training surface or a participant may be presented with a view of the virtual training world with the view changing so as to simulate moving through the virtual training world. In one example, the speed may be represented by how far away an end point of a tile appears. As cadence goes up, the end point appears farther away. As the intensity goes up, the end point appears farther away. A standing position generally corresponds to lower speed and therefore the end point will appear closer. As with inclination (i.e. height of the end point), the apparent distance to the end point may be provided by a lookup table. Optionally, the apparent distance and/or apparent length of a tile may be adjusted if the participant's speed or intensity deviates from the speed or intensity of the interval of the workout plan.

The system further displays at least one feedback indicia to the participant. Examples of feedback indicia include interval markers indicating borders or transitions between sequential intervals of the training surface and one or more of the training parameters of the workout plan. In some examples, interval markers are provided as posts, arches or rings that are beside, over or surround the training surface such that a participant passes by or through a portal as the participant moves to the next interval. The interval markers or portals may be pattern-coded or color-coded to provide information on the next interval. For example, the interval markers may include portions that are red in color to indicate a high-intensity interval. Portions of the training surface may also be color or pattern coded to match the interval markers or to provide additional information. In further examples, the border or transition between intervals may appear visually merely as a change in inclination. Alternatively, the border or transition may not appear on or in the surface, or be indicated by markers, but may instead be indicated by a countdown timer or distance indicator to indicate the time or distance to the next interval.

Figure 1:
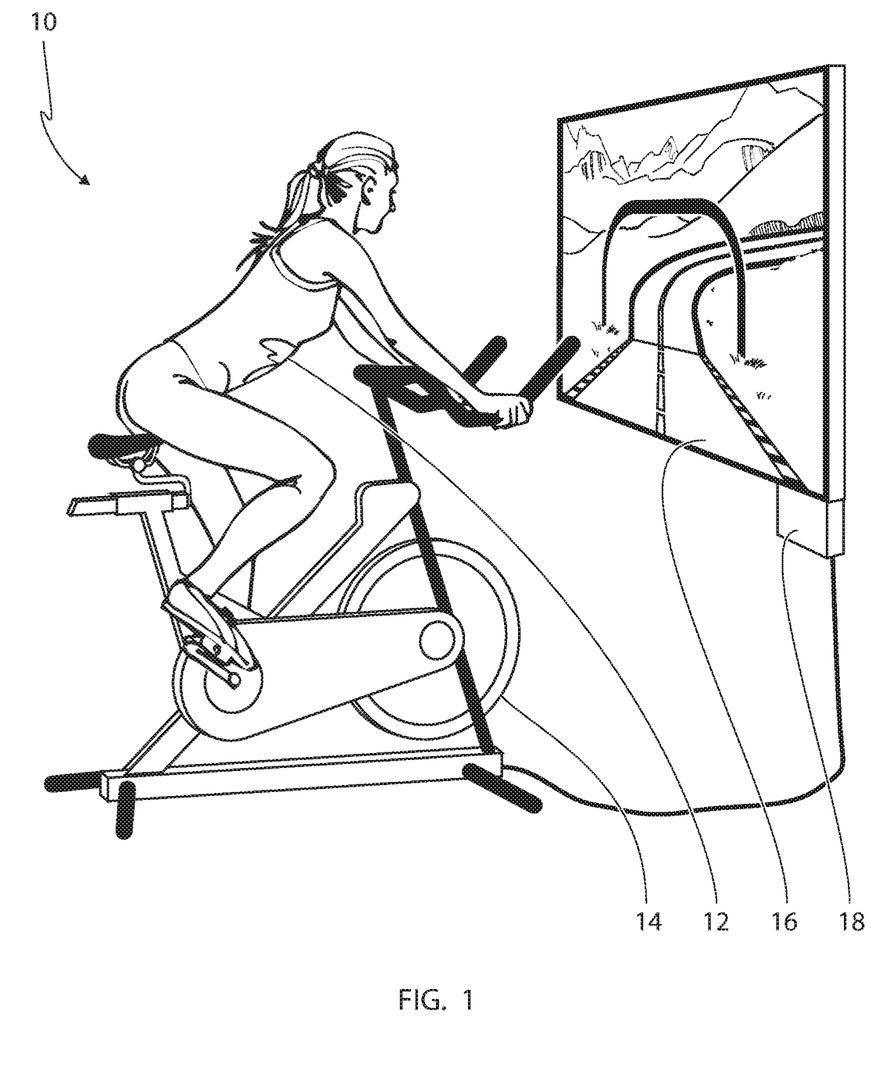
FIG. 1 is a drawing representing a participant on an stationary bike viewing a displaying a visual representation of a virtual training world in accordance with an embodiment of the present invention.

Referring now to FIG. 1, an embodiment of the present invention will be described in more detail. An exercise or training system is illustrated at 10. A participant 12 is riding on a stationary bike 14 that is designed to simulate riding a bicycle, including providing resistance to pedaling. A display 16 displays a visual representation of a virtual training world. In this example, the display is a wall-mounted television screen, but it could also take the form of a display of a telephone, tablet, or computer, a built-in display on the stationary bike 14 or any other form allowing the participant to view the visual representation. A computer 18 is shown attached to display 16. In this example, the computer generates the visual representation of the virtual training world and has a wired connection to the exercise device so as to provide one-way or two-way communication between the exercise device and the computer 18. The computer may take a wide variety of forms, including a stand-alone computer, a phone, a tablet, a laptop, a TV control box (i.e., Apple TV), a computer-integrated into a smart display, or any other type of computing device capable of providing the visual representation to the display. The connection to the display and/or the exercise device may be wired or wireless.

Figure 2:
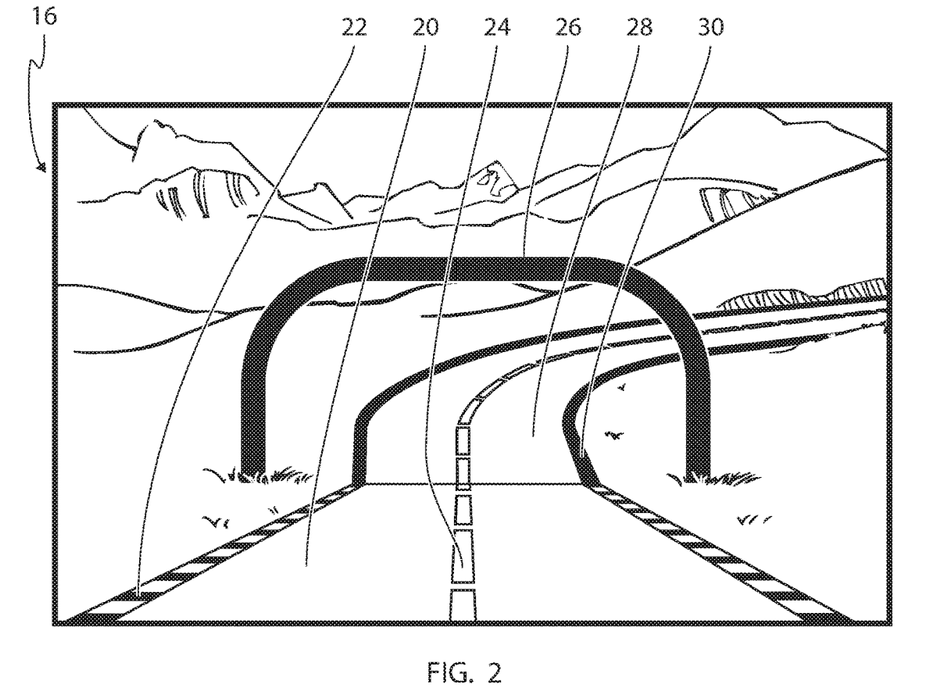
FIG. 2 is a drawing showing a display with a visual representation of the virtual training world.

Referring now to FIG. 2, the visual representation of the virtual training world will be described in more detail. The visual representation is provided on display 16. A virtual training surface 20 is in the foreground of the visual representation such that the participant sees the virtual training surface as being traveled on or along. The virtual training surface may have borders 22 on one or both sides and/or a center line 24, or may lack these features. In this example, the virtual training surface has the appearance of a road with a center line. The border 22 has the appearance of alternating black and white sections. This may be pattern-coded to the corresponding interval to help a participant keep track of where they are along the virtual training surface. Moving from the foreground of the visual representation to the background, the virtual training surface 20 reaches and passes under the interval marker 26. In this example, the interval marker takes the form of an arch 26 extending over the virtual road and indicating the end of the current interval and the start of the next interval. The virtual training surface 28 of the next interval has an upward inclination as compared to the interval in the foreground. This indicates that the interval is a higher intensity interval. In this example, the interval marker 26 is black in color as is the border 30 of the corresponding interval. The foreground interval appears to be straight while the next interval has a training surface 28 that curves. Typically, an exercise device for use with the system does not provide for steering or turns, but instead the visual representation will be updated to show the participant traveling to follow the curves. As discussed previously, world features such as turns may be pseudo-randomly generated such that the path of the virtual training surface may be different every time a participant uses the system. However, the inclination of the training surface is a function of the workout plan and is therefore, in certain embodiments, not randomly generated. Further world features are represented in the background of FIG. 2, including mountains and hills.

Figure 3:
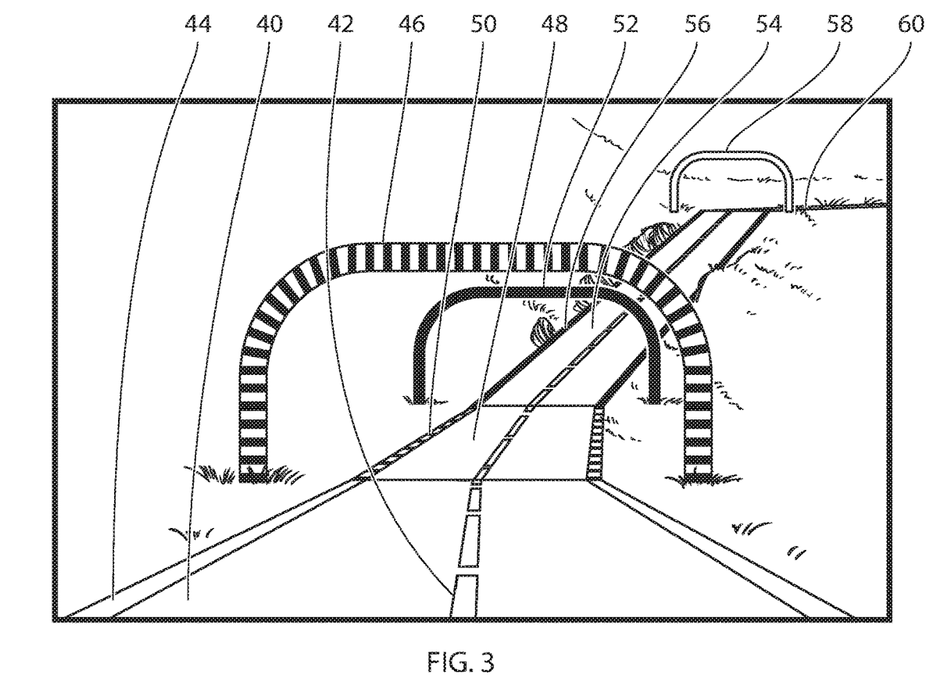
FIG. 3 is a drawing showing a display with another visual representation of the virtual training world.

Referring now to FIG. 3, a plurality of sequential intervals are illustrated. In the foreground, a training surface 40 has a white center line 42 and a white borders 44. An interval marker 46 marks the end of this interval and a start of the next and is pattern-coded with alternating black and white segments. The training surface 48 has borders 50 that are pattern-coded to match the interval marker 46. The training surface 48 appears to be relatively flat, meaning that it is the lower effort interval. The training surface 48 meets a subsequent interval marker 52 after which the training surface 54 inclines upwardly. The interval marker 52 and the borders 56 are both black in color. The training surface 54 reaches a further interval marker 58 that is white in color with a generally flat training surface 60 after this interval marker.

Figure 4:
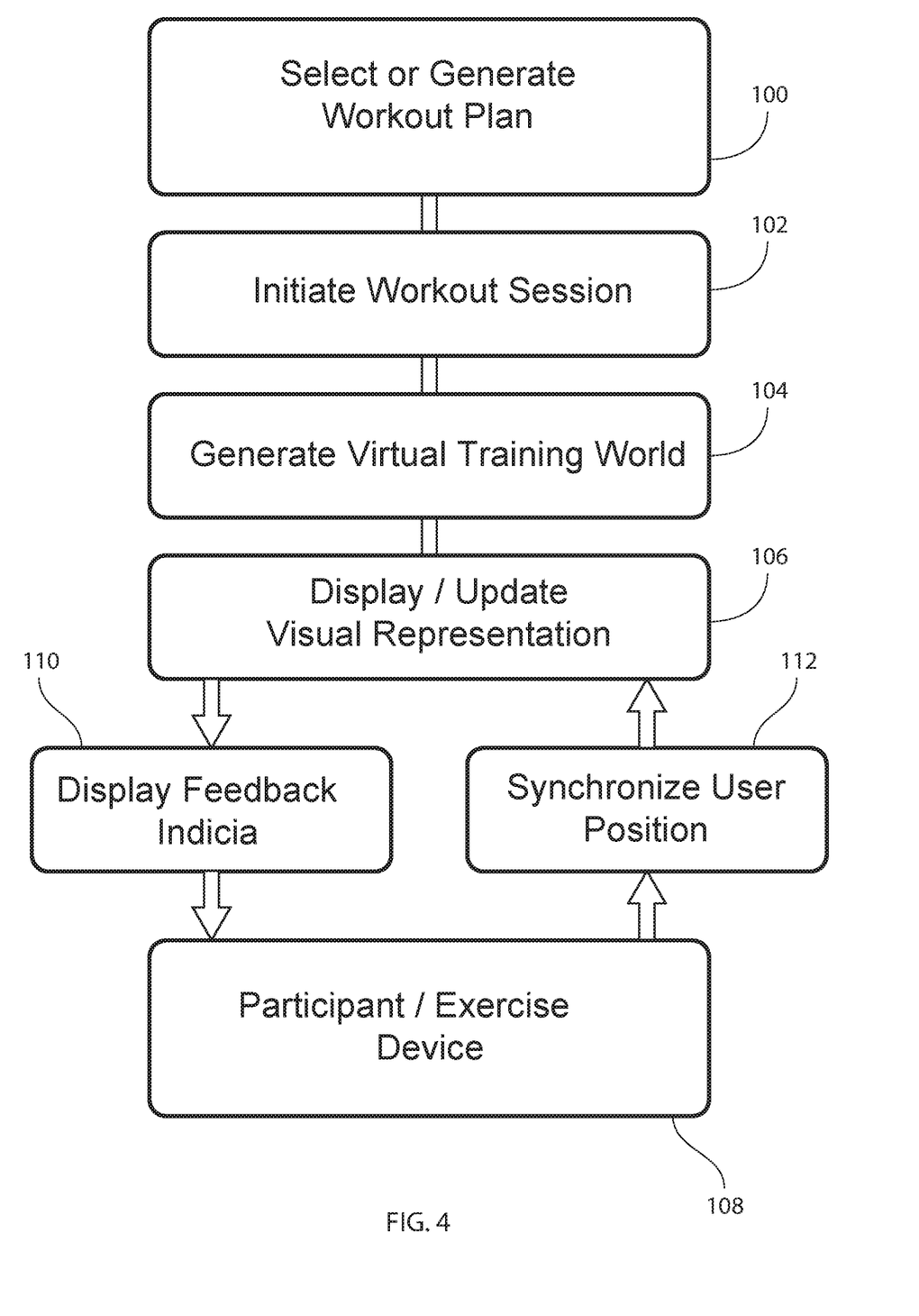
FIG. 4 is a flowchart illustrating an exemplary method in accordance with the present invention.

Referring now to FIG. 4, steps of a method in accordance with embodiments of the present invention will now be described. A participant selects or generates a workout plan at step 100. As discussed earlier, the generation of a workout plan includes defining one or more training parameters for each of a plurality of sequential intervals. Part of selecting or generating a workout plan may include picking a type of training world, such as "under water." "outer space," or "on land." This choice may then determine some of the visual features of the virtual training world. Generating a training plan may include specifying music for one or more intervals, and the music may be adjusted to suit the interval, such as by adjusting the beat of the music to match the chosen pace or intensity.

A participant may then initiate a workout session at step 102 and a virtual training world is generated at 104. The initiating step may include choosing various aspects of the workout, such as duration, music to be played, type of training world (either instead of during the generating step or as an override to the type of training world) and other aspects. In some embodiments, the world is not actually generated until the workout session is initiated while in other embodiments generation may occur earlier, including generating and saving the generated world.

Generation of a virtual training world includes defining an inclination of a training surface for each of the sequential intervals and pseudo-randomly generating a plurality of world features, which may include turns in the training surface and features of the turns. In some examples, the system uses multiple layers to generate all visuals that are all governed by the generation algorithm. The system picks from a pool of different background landscapes, set dressings, roads and sky boxes to match the difficulty of a workout. Additionally, there may be characters such as animals or flying space ships that each have their own generation algorithms and path finding Artificial Intelligence (AI) protocols. A visual effects layer may add more depth to the image. As an example, elements such as water drops or fog are rendered on a camera layer that overlays all other content. Certain embodiments of the present invention use a proprietary algorithm to create a visual representation of a parametric workout. The JSON input, consisting purely of numbers over time, is taken and interpreted by an "AI system". This system is able to connect the parametric values in the given workout source to virtual assets (3D meshes of environment and road) and thus create a visual representation. In order to ensure that the same workout source will always deliver different worlds (to keep the participant excited even when re-visiting workouts) a random seed consisting of five numbers is used. This leads to 99999×99999 possibilities in combination for each individual world that is available and essentially endless, non-repetitive worlds for the participant to experience. The deterministic parts are a function of the defined workout plan. Specifically a training surface is displayed. The training surface has an inclination and turns (the turns may come randomly and are thus randomly generated, or may be deterministic). In essence it is the inclination/profile of the training surface that is a function of the workout plan, i.e. the inclination is a function of RPM, intensity, and position (standing or sitting). The inclination may go up when the RPM goes down. The same may be the case with the intensity. The position may add or subtract to the inclination. For example, a standing position may add to the inclination The AI protocols construct the layers such that elements in the individual layers do not appear to interfere with each other. As an example, the training surface has turns. The path of the training surface may constrict where a layer "behind" the training surface has objects that would otherwise interfere with the training surface.

In an example, each "layer" has a set of objects to randomly choose from. The objects may be placed pseudo-randomly, but the positioning is conditioned on layers that appear in front. The layer at the back may be the horizon, i.e. a background color. If mountains are present, the second layer may be mountains for which the position, size and other features may be pseudo-randomly generated. There may also be a layer with smaller objects such as tree, plants, animals etc. The virtual training surface is a further layer.

A visual representation of the virtual training world is then displayed or updated at step 106. A participant and their exercise device is indicated at box 108 with feedback indicia being provided from the visual representation at box 110 and information on the participant's position or speed being provided back at box 112 so that the visual representation may be updated at box 106.

The background may move at a speed defined by the training session. Therefore, in the visual representation, when one mountain moves out of the picture bit by bit a new mountain starts to come into the picture.

Figure 5:
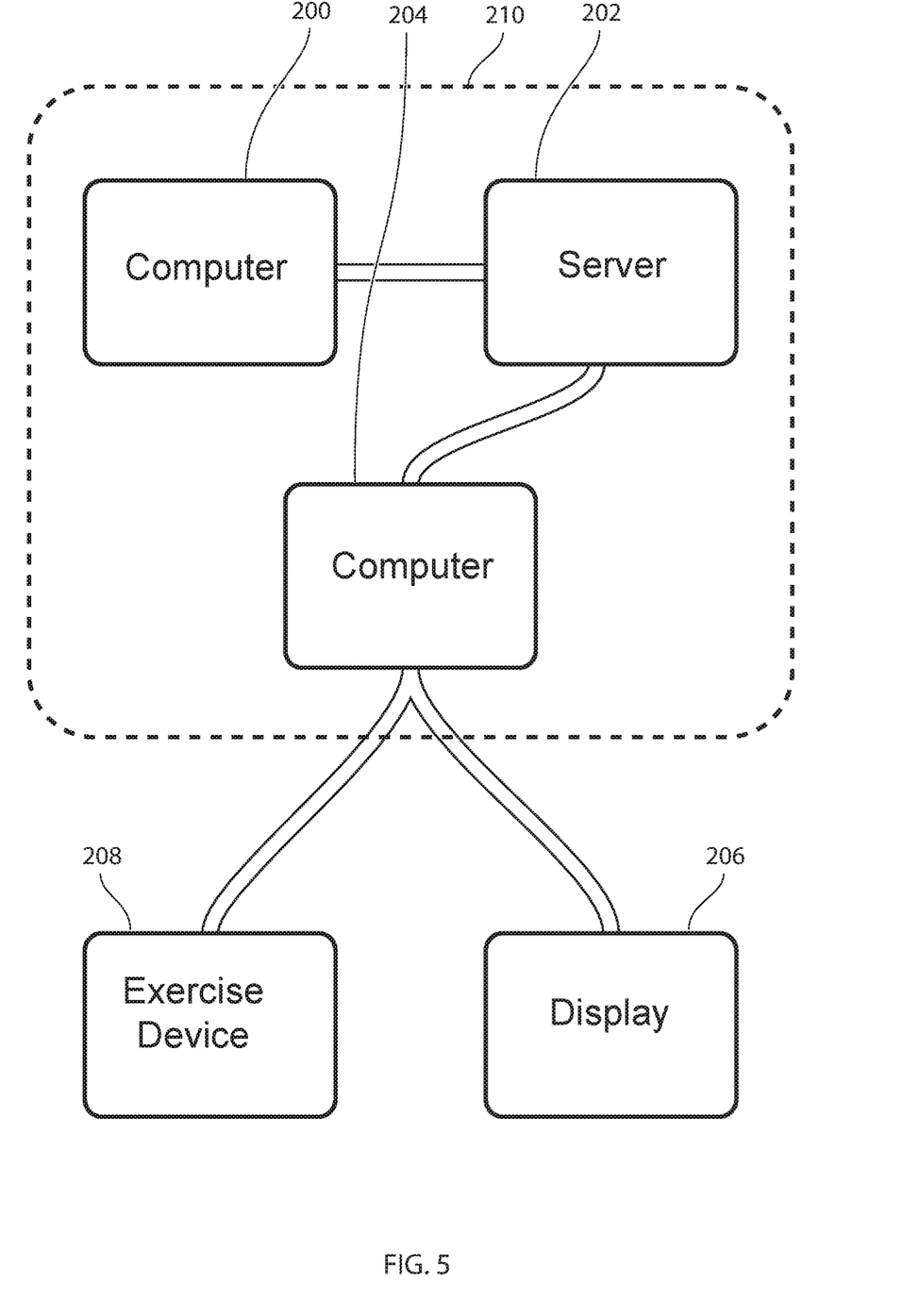
FIG. 5 is a schematic representing a system in accordance with an embodiment of the present invention.

FIG. 5 provides a schematic of a system for practicing embodiments of the present invention. A first computer is shown at 200 and may be used for the step of selecting or generating a workout plan. Such a computer may be a stand-alone computer, a laptop, a phone, a table or other computing device. The selecting or generating of a workout plan may take place on this computer, or the computer 200 may be in communication with a server 202. For example, the software associated with the method may run on a server or servers and be accessed by computer 200 via a webpage. A virtual training world may be generated on the server 202 or on the computer 200. A computer 204 is connected to a display 206 for displaying the visual representation of the virtual training world. The computer 204 may also connect to the exercise equipment 208, for embodiments of the present invention where information is provided between the exercise device and the system. Any of the connections between the various computers and other equipment may be wired or wireless. Box 210 indicates that one or more of the computers 200, 202 and 204 may be a single device performing more than one of the method steps. For example, all computing functions may take place on the server with the display merely displaying what information is provided for the server. However, typically a computer 204 will control the display and may take the form of computer, laptop, phone, tablet, smart TV, or control box for a TV. The exercise equipment 208 may take a variety of forms, including a stationary exercise bike, such as illustrated at 14 in FIG. 1, a bike trainer, or a treadmill. A biker trainer is a device that connects to the rear wheel or drivetrain of an actual bicycle and provides resistance for the participant. The computer 204 may control the resistance of the bike trainer, exercise bike or treadmill, with the treadmill resistance typically be in the inclination of the treadmill belt. Alternatively, the display 206 may provide information to the participant indicating a resistance or intensity level to be used, with the participant manually adjusting the exercise equipment. The display 206 may take a variety of forms, including a computer display, TV, tablet, phone, headset or a display that forms part of the exercise bike or treadmill.

Figure 6:
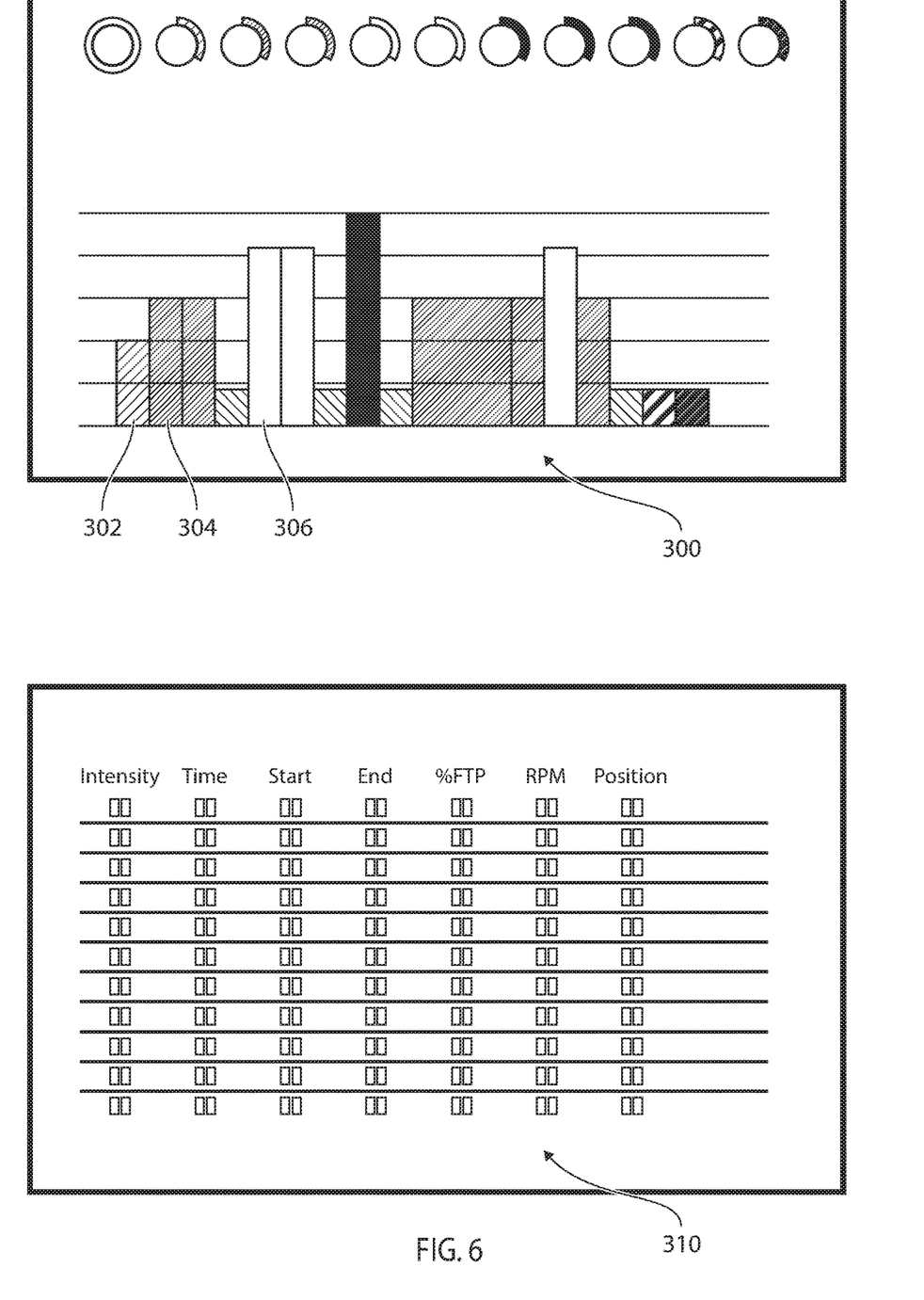
FIG. 6 is a drawing representing software for generating a workout plan, which may form part of the present invention.

Referring now to FIG. 6, an example of generating a workout plan will be described. FIG. 6 is a visual representation of a webpage on which a workout plan may be defined. A plurality of colored bars 300 each indicate an interval with the height of the interval indicating an intensity level and a width of the bar indicating duration. A participant defines one or more training parameters for a first interval 302, then for a second interval 304, etc. Preferably, the webpage allows the participant to adjust intervals by picking and stretching an interval up or the side to change intensity and width. Training parameters may also be added. Interval 306 has a bar near the top indicating, in this example, that this is a standing interval. A chart 310 is provided below the bar 300 and includes various training parameters for each of the intervals. A participant may adjust these parameters by changing the data entries in the chart.

As will be clear to those of skill in the art, the embodiments of the invention described herein may be altered in various ways without departing from the scope or teaching of the present invention. It is the following claims, including all equivalents, which define the scope of the invention.

The invention claimed is:

1. A method for providing a training system having an interactive training environment for athletic activities performed on an exercise device with variable resistance levels, the method comprising the steps of:
   on a computer;
      selecting or generating a workout plan having a plurality of sequential intervals, each interval having at least one training parameter associated therewith, the at least one training parameter including an intensity;
      generating and displaying a visual representation of a new virtual training world including a virtual training surface;
         the training surface divided into a plurality of sequential intervals;
         each interval having an inclination that is a function of the at least one training parameter associated with a respective one of the intervals of the workout plan;
         each interval comprising a segment or multiple segments, each segment representing a certain distance and having a start point and an end point, a height of the end point being how high the end point appears relative to the start point, wherein the function comprises defining the height of the endpoint of each segment relative to the start point;
         the virtual training world further having a plurality of visual world features including at least turns in the training surface, at least some of the plurality of visual world features being pseudo-randomly generated each time a new virtual training world is generated;
      wherein displaying the visual representation further includes representing a participant position of a participant in the virtual training world;
      synchronizing the participant position in the virtual world based on a speed of and/or distance traveled by the participant and/or an elapsed time; and
      displaying at least one feedback indicia to the participant, the feedback indicia being selected from interval markers indicating borders or transitions between the sequential intervals of the training surface and one of the training parameters.

2. The method according to claim 1, wherein the at least one training parameter further includes a pace and/or an exercise position.

3. The method according to claim 2, wherein the pace is an RPM or a cadence and the exercise position comprises a seated position or one or more standing positions.

4. The method according to claim 1, wherein the feedback indicia include the interval markers, the interval markers being color-coded and/or pattern-coded to differentiate the intervals.

5. The method according to claim 4, wherein the training surface following each interval marker is at least partially color-coded or pattern-coded to match the corresponding interval marker.

6. The method according to claim 1, wherein the training surface at the end of each of the sequential intervals continuously and smoothly transitions into the training surface of a beginning of a next one of the sequential interval.

7. The method according to claim 6, wherein the training surface of at least the next one of the sequential intervals being displayed to the participant when the participant position is in a current one of the sequential intervals.

8. The method according to claim 1, further comprising initiating, by the participant, a selected or generated workout session, the generating a new virtual training world step being performed after the initiating step and before the displaying step.

9. The method according to claim 1, wherein the step of selecting or generating a workout comprises generating a workout by defining the plurality of sequential intervals, the at least one training parameter associated with at least some of the intervals including the intensity, an RPM or cadence, and an exercise position.

10. The method according to claim 1, further comprising providing from the computer an intensity signal operable to adjust the variable resistance levels of the exercise device.

11. The method according to claim 1, wherein the feedback indicia further include at least one of total training time, time remaining in interval, time remaining in workout, target RPM, target RPM range, target intensity, exercise position, resistance level of the exercise device, actual participant RPM, actual participant heart rate, and actual participant wattage.

12. The method according to claim 1, wherein the step of displaying feedback indicia includes displaying an intensity level corresponding to the inclination of the training surface.

13. The method according to claim 1, further comprising receiving by the computer a signal from the exercise device representing a speed or and/or a distance traveled by the participant.

14. The method according to claim 1, wherein the visual world features further include at least one feature selected from a group consisting of weather, wind, animals, plants, landscape features and people.

15. The method according to claim 1, wherein the inclination is a function of intensity, pace and position.

16. The method according to claim 1, wherein the computer further includes an AI system configured to interpret the at least one training parameter and associate the at least one training parameter to the training system and the plurality of visual world features.

17. The method according to claim 1, wherein the selecting or generating a workout plan comprises generating a workout plan and saving the workout plan.

18. The method according to claim 1, wherein displaying the visual representation is implemented on a second computer.

19. The method according to claim 1, wherein the at least some of the plurality of visual world features being pseudo-randomly generated includes the turns.

20. The method according to claim 1, wherein the height is determined from a lookup table.

21. An apparatus for providing a training system having an interactive training environment for athletic activities performed on an exercise device with variable resistance levels, the apparatus comprising:
   a memory; and
   at least one processor, coupled to the memory, operative to:
      select or generate a workout plan having a plurality of sequential intervals, each interval having at least one training parameter associated therewith, the at least one training parameter including an intensity;
      generate and display a visual representation of a new virtual training world including a virtual training surface;

the training surface divided into a plurality of sequential intervals;

each interval having an inclination that is a function of the at least one training parameter associated with a respective one of the intervals of the workout plan;

each interval comprising a segment or multiple segments, each segment representing a certain distance and having a start point and an end point, a height of the end point being how high the end point appears relative to the start point, wherein the function comprises defining the height of the endpoint of each segment relative to the start point;

the virtual training world further having a plurality of visual world features including at least turns in the training surface, at least some of the plurality of visual world features being pseudo-randomly generated each time a new virtual training world is generated;

wherein display of the visual representation further includes representing a participant position of a participant in the virtual training world;

synchronize the participant position in the virtual world based on a speed of and/or distance traveled by the participant and/or an elapsed time;

display at least one feedback indicia to the participant, the feedback indicia being selected from interval markers indicating borders or transitions between the sequential intervals of the training surface and one of the training parameters.

\* \* \* \* \*